United States Patent [19]
Cailleteau

[11] Patent Number: 5,745,926
[45] Date of Patent: May 5, 1998

[54] SAFETY BAG, IN PARTICULAR FOR HYGIENIC PURPOSES

[76] Inventor: Benoît Cailleteau, 97 Avenue du Prado, 13008 Marseille, France

[21] Appl. No.: 745,817

[22] Filed: Nov. 12, 1996

[51] Int. Cl.$^6$ .................................................. A47K 11/12
[52] U.S. Cl. .................. 4/144.1; 4/144.3; 604/350; 383/44; 128/767
[58] Field of Search ............................... 4/144.1, 144.2, 4/144.3, 144.4; 604/349, 350, 329; 128/767; 383/43, 44

[56] References Cited

U.S. PATENT DOCUMENTS

| | | | |
|---|---|---|---|
| 2,080,402 | 5/1937 | Herman | 383/43 |
| 2,665,033 | 1/1954 | Robertson | 383/43 |
| 2,875,451 | 3/1959 | Stegeman | 4/144.1 |
| 3,403,410 | 10/1968 | Benzel et al. | 4/144.2 |
| 3,403,715 | 10/1968 | Trudel | 150/9 |
| 3,724,461 | 4/1973 | Eisenberg | 383/35 |
| 3,926,233 | 12/1975 | Brendling | 604/350 |
| 4,261,253 | 4/1981 | Smith, II | 493/189 |
| 4,804,377 | 2/1989 | Hanifl et al. | 4/144.3 |
| 5,056,932 | 10/1991 | Young | 383/36 |
| 5,569,225 | 10/1996 | Fleury | 604/349 |

FOREIGN PATENT DOCUMENTS

| | | |
|---|---|---|
| 2249132 | 4/1973 | Germany. |
| 2936622 | 3/1981 | Germany. |

*Primary Examiner*—Charles R. Eloshway
*Attorney, Agent, or Firm*—Ostrolenk, Faber, Gerb & Soffen, LLP

[57] ABSTRACT

A safety bag of flexible material such as a thin sheet of transparent plastics material, the bag having an opening of dimensions appropriate for its use with an edge that is suitable for being bonded to reinforcement for facilitating the opening of a passage to the inside of the bag starting from a flattened position in which the opening is closed, said bag also including a first tubular element bonded in leakproof manner to the bag in the vicinity of its opening and extending into the bag from its opening over an appropriate distance, e.g. about 15 cm. A second tubular element is disposed between the facing walls of the bag and of the first tubular element, second tubular element being also bonded in leakproof manner to the bag in the vicinity of its opening and extending to the inside of the bag over a distance greater than that of the first element.

6 Claims, 2 Drawing Sheets

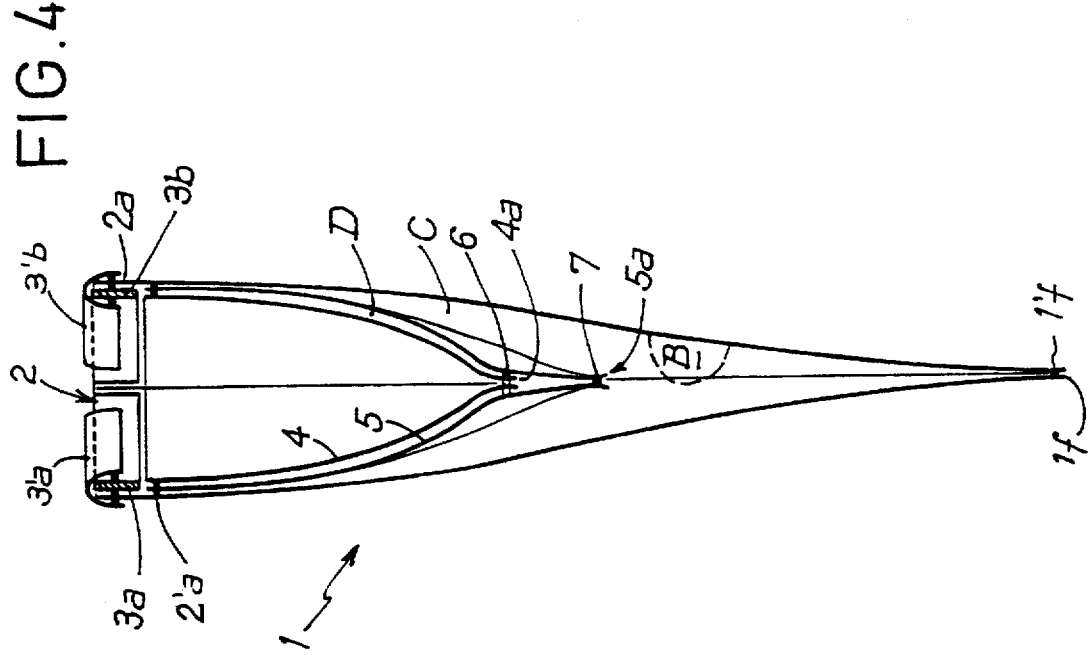
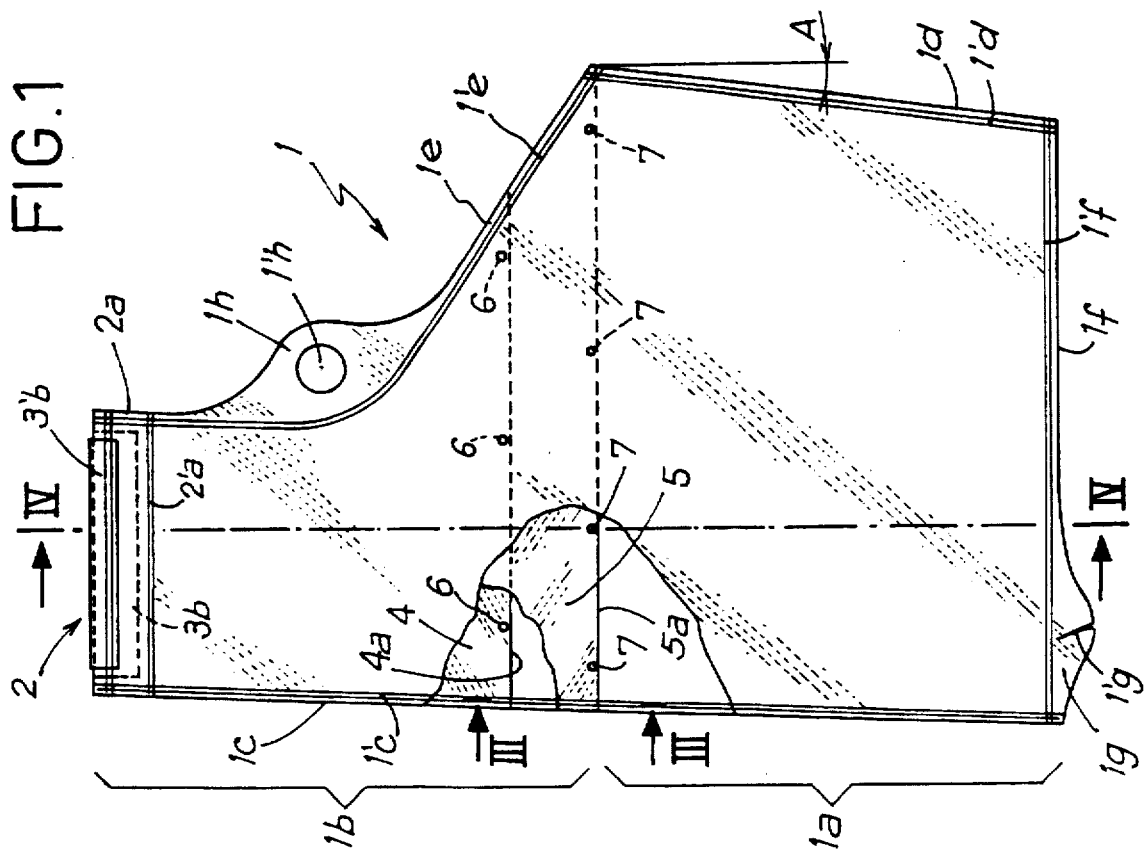

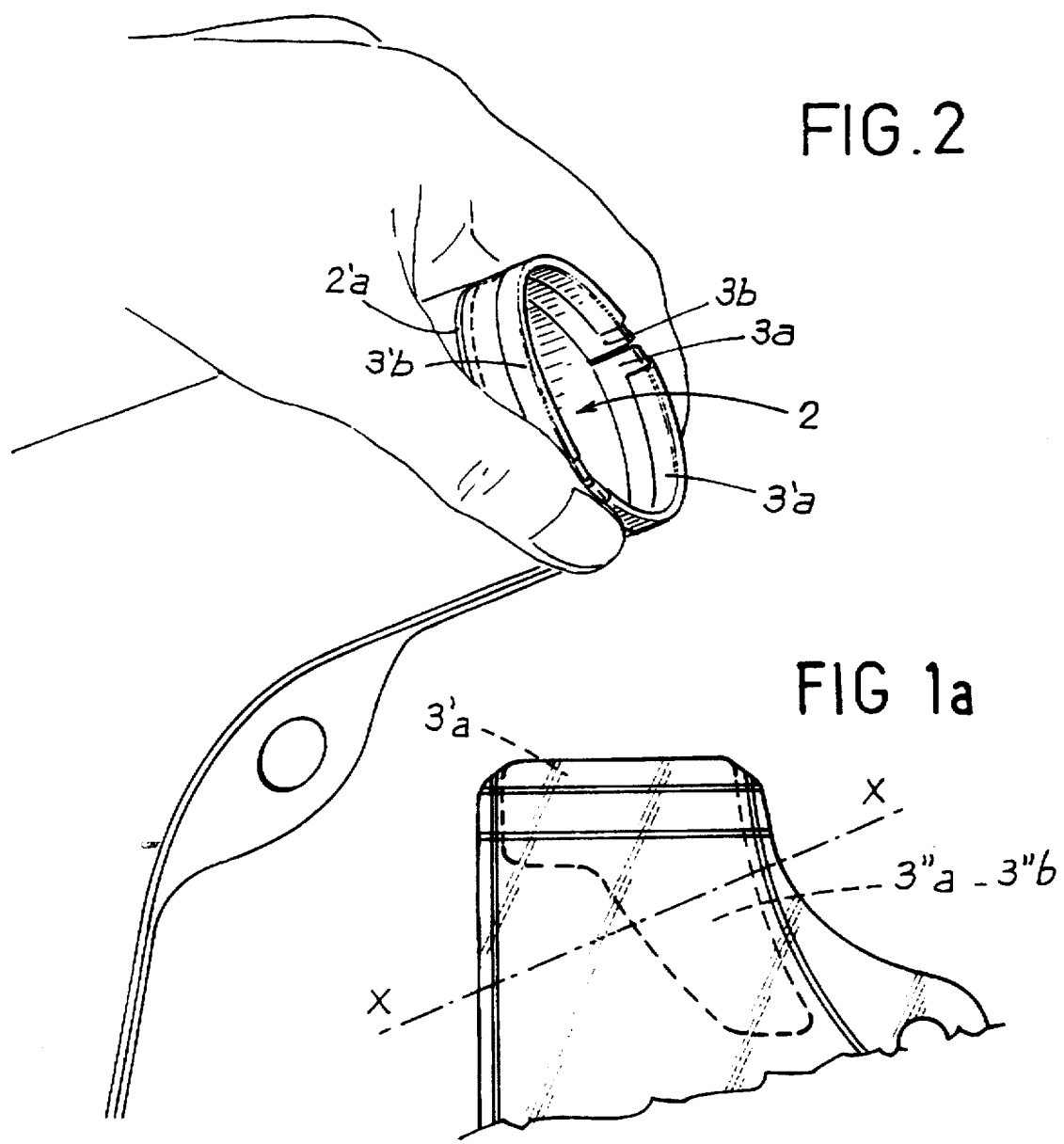
FIG. 2
FIG 1a
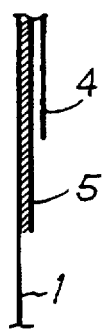
FIG. 3a
FIG. 3b
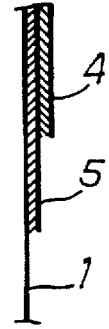
FIG. 3c

SAFETY BAG, IN PARTICULAR FOR HYGIENIC PURPOSES

The present invention relates to a safety bag of flexible material for receiving waste of various origins, in particular of human origin, and under particularly hygienic conditions. Bags of this kind are already known, generally presented in flattened form and intended for use to collect urine or vomit, for example. In this respect, mention may be made of the flexible bags described in published documents DE-A-2 515 159, FR-A-2 169 957, GB-A-2 227 728, or indeed EP-A-591 144 (WO 91/03994), and those constituting the subject matter of DE-A-2 936 622 or 2 949 132 or, indeed U.S. Pat. Nos. 4,261,253 and 5,056,932.

BACKGROUND OF THE INVENTION

Such bags are made of thin sheets of paper or plastics material, they are optionally transparent, and they have an opening of dimensions appropriate for their function. In some cases, the rim of the opening is associated with reinforcement suitable for being deformed by the user starting from the flat position so as to make it easier to open up a passage to the inside of the bag. In addition, known safety bags are generally equipped with a device for preventing untimely egress of the substances that have been inserted therein, particularly if those substances are liquid. Thus it is common to provide a kind of non-return valve constituted merely by one or two tubular elements generally made of flexible material analogous to that used for the bag itself. These elements are connected in sealed manner to the bag in the vicinity of its opening and they extend axially into the bag from its opening over an appropriate distance. When the substances received in the bag in question are liquid, the axial length of the tubular elements is about 10 cm, and generally a little longer, with the inner tubular element being axially shorter than the tubular element adjacent to the inside walls of the bag.

It has nevertheless been observed that the above-outlined dispositions are insufficient to ensure under all circumstances that a safety bag remains sealed after use, particularly when it is intended to receive liquids and a high degree of hygiene is essential. This applies in particular if the bag is used as a urinal, e.g. in a hospital, and at least one of the tubular elements is in the form of a funnel.

OBJECTS AND SUMMARY OF THE INVENTION

The present invention seeks to remedy the observed drawbacks of known hygienic bags while seeking to provide a product that is easy and cheap to manufacture, given the frequent need to discard or destroy it after use.

The invention thus relates to a safety bag as defined in the preamble of claim 1.

According to a first characteristic of the invention, the internal transverse edges of the tubular elements extend transversely over substantially the entire width of the bag when it is in its flattened position.

Because of this disposition, the non-return valve effect provided by the tubular elements is greatly improved and the substances, in particular liquids, inserted into a bag can no longer escape therefrom whatever movements are applied to the bag or whatever the position in which it is placed, and there is no risk of back flow while said substances are being inserted into the bag.

Various secondary dispositions may be provided to make the non-return valve effect sealing the opening of the bag even more effective, and they are described below.

BRIEF DESCRIPTION OF THE DRAWINGS

The invention will therefore be better understood and its secondary characteristics and advantages will appear on reading the following description of an advantageous embodiment intended more particularly for use as a urinal usable in circumstances requiring a high degree of hygiene and possibly even of asepsis. To this end, reference is made to the accompanying drawings, in which:

FIG. 1 is an elevation view of a safety receiving bag of the invention;

FIG. 1a is a fragmentary elevation view of an embodiment of the neck of the bag;

FIG. 2 is a perspective view on a larger scale of the opening region of the bag shown in FIG. 1;

FIGS. 3a, 3b, and 3c are diagrammatic sections on III—III of FIG. 1 showing three possible embodiments of the region of a side edge of the bag in its flattened position; and FIG. 4 is a diagrammatic section on IV—IV of FIG. 1 with the opening of the bag being assumed to be in the position shown in FIG. 2.

MORE DETAILED DESCRIPTION

Although the description which follows and the accompanying drawings relate to a bag having only two tubular elements, the invention is naturally not limited to bags of that type. More precisely, the bag must include at least two valve-forming tubular elements.

With reference initially to FIGS. 1 and 2, there can be seen a safety bag 1 designed to be used as a urinal, constituted by a thin sheet of transparent plastics material and having an opening given general reference 2. The shape of the bag is not determined by the invention, but in the example shown it comprises a working portion 1a which, in the flattened position shown in FIG. 1, is substantially rectangular, ignoring the exception explained below. The working portion 1a of the bag is connected to the opening 2 via a portion 1b having any appropriate profile. Preferably, and as can be seen in FIG. 1, one of the side edges 1c of the bag is substantially rectilinear and extends perpendicularly from the opening 2 over the combined length of the portions 1a and 1b of the bag. In contrast, the edge diametrically opposite to the edge 1c comprises a substantially rectilinear segment 1d in the portion 1a of the bag and a curvilinear segment 1e connecting to the opening 2 in the portion 1b.

It can already be specified that the segment 1d advantageously extends away from the opening 2 so as to form an acute angle A with the edge 1c. Also, the bag 1 is easily made either from a tube of thin transparent plastics material or from superposed sheets. In either case, at least one of the edges 1c and 1d and also the bottom if and the curvilinear segment 1e are advantageously defined by lines of heat sealing 1'd, 1'e, and 1'f between the two walls of the bag, performed either before or after the outside profile of the bag has been cut out.

It is also mentioned at this point that the bottom if is advantageously cut so as to have a tab 1g extending beneath the heat seal line 1'f. A notch 1'g is formed in the tab 1g but without extending as far as the heat seal line 1'f. Similarly the segment 1e has a tab 1h situated beyond the heat seal 1'e and including a hole 1'h. The purposes of these various auxiliary dispositions appear below.

With reference now to FIGS. 1, 2, and 4, it can be seen that the opening 2 of the bag is constituted by a sleeve 2a that is suitable, like the bag itself, for occupying a flattened position. Reinforcement constituted by two relatively rigid but flexible blades 3a and 3b is secured inside the bag. Although the invention does not relate in any way to the reinforcement and the manner in which it is connected to the edge of the opening, it appears to be advantageous for the blades 3a and 3b to be heat sealed to the inside wall of the sleeve, preferably by strips 3'a and 3'b of flexible plastics material (FIG. 4).

As can be seen in FIG. 1a, it is also desirable for the blades to have axial extensions 3"a and 3"b extending a suitable distance into the inside of the bag, e.g. over two to five times the width of the blades. These extensions may be partial as shown, or they may correspond to the entire transverse width of the neck of the bag.

Two "tubular elements" are disposed inside the bag 1 and given overall references 4 and 5. They are constituted by thin sheets of transparent plastics material, preferably thinner than the material constituting the bag 1 itself.

As can be seen clearly in FIG. 4, a first tubular element 4 extends into the inside of the bag from a region close to the edge of the opening 2, i.e. the sleeve 2a. The element 4 is bonded in sealed manner to the bag 1, e.g. by heat sealing to the sleeve 2a along a continuous line 2'a all around the sleeve. The second tubular element 5 is disposed between the facing walls of the bag 1 and is also fixed in sealed manner to the bag 1, more specifically to its sleeve 2a, by a line of heat sealing that preferably coincides with the above-mentioned line 2'a. Thus, in the region of the sleeve 2a close to the edge of the opening 2, there exists no possible pathway between the bag 1 and one or other of the tubular elements 4 and 5 for any substances and in particular for any liquids that may be contained in the bag 1.

The first tubular element 4 extends inside the bag over an appropriate length which is generally close to 10 cm and preferably not less than 15 cm even though the second element 5 itself extends over a greater length, e.g. a length that is 2 cm longer than the first tubular element.

As mentioned above with reference to the bag 1 itself, the tubular elements can be made from tubes of appropriate diameter or they can be made from superposed sheets. In either case, when in the flattened position shown in the drawings, the lateral edges of the elements facing the edges 1c and 1e of the bag are, if necessary, closed by axially extending lines of heat sealing. Nevertheless, it is preferable, as shown in the drawings, for the lateral edges of the tubular elements to be cut to match the shapes of the edges 1c and 1e and to be assembled to said edges along common lines of heat sealing 1c and 1e (FIG. 3c).

In any event, and as already emphasized, it can be seen that it is important for the internal transverse edges 4a and 5a of the tubular elements to extend transversely over the major portion of the width, and if possible over the full width, of the bag 1 when it is in its flattened position (FIG. 1).

Nevertheless, depending on the structure of the tubular elements when they are fixed to the bag, for example if they are constituted by tubes of plastics material having dimensions close to those of the opening 2, it is necessary only for at least one of the lateral edges of the element 5 to be fixed to the bag 1 (FIG. 3a) or indeed for only at least one of the lateral edges of the element 4 to be fixed to the corresponding lateral edge of the element 5 (FIG. 3b).

It is also highly advantageous for localized bonds to be provided in the vicinity of the internal transverse edges 4a and 5a of the tubular elements between the walls of said elements which face one another when the bag 1 is in its flattened position. These localized bonds are preferably constituted by heat sealing points 6 or 7 located in alignment along each transverse edge. The heat sealing points 6 situated along the transverse edge 4a serve at least to hold together the two walls constituting the tubular element 4 and preferably also to hold them to the walls of the element 5. Naturally, along the transverse edge 5a, the points of heat sealing 7 serve only to assemble together the two walls of the element 5.

With reference to FIG. 1, it must nevertheless be emphasized that the localized bonds 6 of the line situated in the vicinity of the edge 4a are axially staggered relative to the localized bonds 7 in the line situated in the vicinity of the edge 5a.

These localized bonds do not significantly alter the useful width of the opening of the valve 4–5 in the bag, and consequently they do not increase in any way the risk of back flow occurring when substance is inserted into the bag.

Because of these dispositions taken together, substances and in particular liquids inserted into the bag 1 are held captive therein whatever movement may be imparted to the bag or whatever the position in which it may be placed. The liquid contained in the bag cannot engage along the internal edge 4a between the facing walls of the element 4 because of the localized bonds 6 between those two walls, given the additional presence of the localized bonds 7 along the internal edge 5a between the walls of the element 5. As can be seen on examining FIG. 4, any mass of liquid contained in the bag 1 can move only in the space C situated between the walls of the bag 1 and the element 5, and closed at the line of heat sealing 2'a. Furthermore, should a small quantity of liquid manage to penetrate into the space situated between the walls of the elements 4 and 5, it will necessarily be held captive in the space D that is also closed at the line of heat sealing 2'a.

In certain applications of the bag of the type described, it may nevertheless be desirable to be able to empty out the substance contained in the bag before discarding it. To this end, the tab 1g (FIG. 1) and its notch 1'g enable the bag 1 to be ripped open from beyond the line of heat sealing 1'f, after which it can be emptied.

In contrast, if it is desired to conserve, at least temporarily, the bag together with the substances it contains, the hole 1'h in the tab 1h (FIG. 1) enables the bag to be suspended from any appropriate support.

Also, it may be observed that because of the above-specified inclination between its two lateral edges 1c and 1d (FIG. 1) the full bag can rest without any danger of spilling on a horizontal plane parallel to its edge 1d.

Finally, it is mentioned that the axial extensions 3"a and 3"b of the blades 3a and 3b serve to prevent the bag folding while it is in use, e.g. along a line X—X (FIG. 1a), thereby constituting a pseudo-tube that would be liable to give rise to troublesome back flow.

Naturally, any appropriate appendix may be placed in the opening 2 for various specific uses of the bag and can be held therein by the reinforcement 3a–3b or can even replace the reinforcement (FIGS. 1 and 2).

Finally, it is recalled that the bag of the invention may include more than two valve-forming tubular elements and that the above-described dispositions can be applied without difficulty by the person skilled in the art to any number of tubular elements. In practice, it generally seems that three or four tubular elements suffice.

I claim:

1. A safety bag intended for use for hygienic purposes, in particular as a urinal, the bag being comprised of flexible sheet material and having first and second facing walls defining between them an inside of the bag, the bag further having an inlet which has an edge suitable for being bonded to reinforcement means adapted to facilitate the opening of the inlet from a flattened positioned of the bag in which the inlet is closed, the bag also including a first tubular element and at least one second tubular element, each of which comprises sheet material and having a first and a second wall, the first and second walls of said at least one second tubular element being respectively disposed between the first wall of the bag and the first wall of the first tubular element and between the second wall of the bag and the second wall of the first tubular element, said tubular elements being bonded in a leakproof manner to the bag proximate the inlet thereof, said tubular elements extending in a longitudinal direction of the bag from the inlet of the bag into the inside thereof and having respective internal transverse edges opposite the inlet of the bag, a distance between said inlet and the internal transverse edge of the at least one second tubular element being greater than the distance between the inlet and the internal transverse edge of the first tubular element, the internal transverse edges of the tubular elements extending transversely substantially over an entire width of the bag in the flattened position thereof, a first line of discrete, localized bonds along the internal transverse edge of the first tubular element bonding the walls of said first tubular element together and to the walls of the at least one second tubular element, and a second line of discrete, localized bonds along the internal transverse edge of the at least one second tubular element bonding the walls of said at least one second tubular element together.

2. A bag as claimed in claim 1, wherein the discrete, localized bonds in the first line are in positions that are staggered relative to the positions of the discrete, localized bonds of the second line.

3. A bag as claimed in claim 1, wherein, in the flattened position of the bag, said bag defines a first lateral edge that extends substantially perpendicularly to the edge of the inlet and a second lateral edge having a first part which is proximate the inlet and a second part which extends from the first part, said second part extending so as to form an acute angle with a line parallel to the first lateral edge.

4. A bag as claimed in claim 1, wherein, in the flattened position of the bag, at least one of the tubular elements is fixed to the bag along a line starting from the edge of the inlet of the bag and extending substantially up to the internal transverse edge of said at least one of the tubular elements.

5. A bag as claimed in claim 1, wherein, in the flattened position of the bag, the first tubular element is fixed to said at least one second tubular element along a line starting from the edge of the inlet of the bag and extending substantially up to the internal transverse edge of said first tubular element.

6. A bag as claimed in claim 5, wherein said at least one second tubular element is further fixed to the bag.

* * * * *